United States Patent [19]

Bamberg et al.

[11] Patent Number: 4,956,179

[45] Date of Patent: Sep. 11, 1990

[54] ANTIBACTERIAL COMBINATION OF PENICILLIN AND CEPHALOSPORIN

[75] Inventors: Peter Bamberg, Zürich, Switzerland; Bertil A. Ekström, Södertälje, Sweden; Ulf E. Forsgren, Södertälje, Sweden; Berndt O. H. Sjöberg, Södertälje, Sweden

[73] Assignees: Astra Lakemedel Aktiebolag; Astra Pharmaceutical Products, Inc., both of Sweden

[21] Appl. No.: 69,787

[22] Filed: Jul. 2, 1987

Related U.S. Application Data

[63] Continuation of Ser. No. 589,926, Mar. 15, 1984, abandoned, which is a continuation of Ser. No. 464,157, Apr. 25, 1974, abandoned, which is a continuation-in-part of Ser. No. 302,423, Oct. 31, 1972, abandoned.

[30] Foreign Application Priority Data

Nov. 1, 1971 [GB] United Kingdom ............... 50657/71

[51] Int. Cl.$^5$ ............................................. A61K 35/66
[52] U.S. Cl. ..................................................... 424/114
[58] Field of Search ............................................ 424/114

[56] References Cited

U.S. PATENT DOCUMENTS 4,221,781 9/1980 Bamberg et al. ................. 424/114

OTHER PUBLICATIONS

Chemical Abstracts, 75:49070k (8/16/71).
The Merck Index, 8th ed, 1968, Merck & Co. Inc., Rahway, N.J., p. 222.

Primary Examiner—Jerome D. Goldberg
Attorney, Agent, or Firm—George M. Gould; Bernard S. Leon

[57] ABSTRACT

An antibacterial synergistic composition consisting essentially of a mixture of a penicillin or cephalosporin derivative of the formula

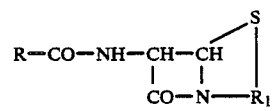

and a penicillin of the formula

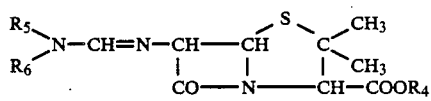

preferably in association with a pharmaceutical carrier.

8 Claims, No Drawings

ANTIBACTERIAL COMBINATION OF PENICILLIN AND CEPHALOSPORIN

This is a continuation of application Ser. No. 589,926 filed Mar. 15, 1984, abandoned which is a continuation application of Ser. No. 464,157, filed Apr. 25, 1974, now abandoned, which in turn is a continuation-in-part application of Ser. No. 302,423, filed Oct. 31, 1972, now abandoned.

This invention relates to new antibacterial synergistic compositions containing penicillin derivatives or cephalosporin derivatives, methods for the preparation of such compositions and a method for the treatment of infectious diseases.

In particular, this invention relates to an antibacterial synergistic composition consisting essentially of a mixture of:

(a) a known, clinically useful penicillin or cephalosporin of the formula

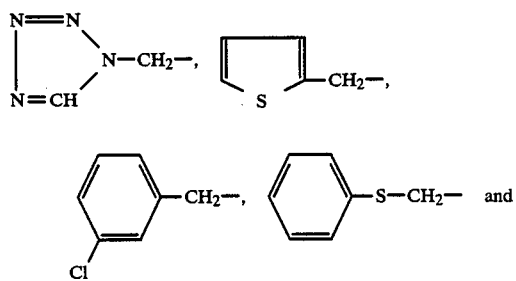
I wherein R is a residue of an organic acid, the residue being selected from the group consisting of $NC-CH_2-$,

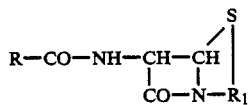

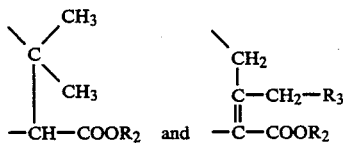

wherein X is selected from the group consisting of $-H$, $-NH_2$, $-N_3$, $-COOH$ and $-SO_3H$, and wherein $R^1$ is selected from the group consisting of the bivalent radicals

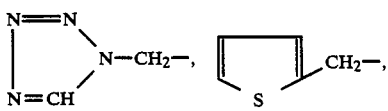

wherein $R_2$ is hydrogen, a pharmaceutically acceptable cation or an in vivo rapidly hydrolyzed pharmaceutically acceptable ester group, and wherein $R_3$ is selected from the group consisting of $H-$, $CH_3COO-$, $N_3-$,

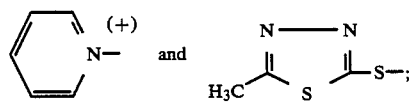

and (b) a known, clinically useful penicillin of the formula

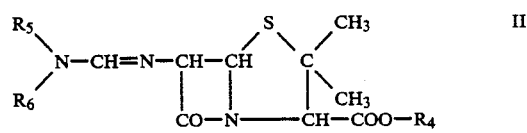
II wherein $R_4$ is hydrogen, a pharmaceutically acceptable cation or an in vivo rapidly hydrolyzed pharmaceutically acceptable ester group, and wherein $R_5$ and $R_6$ are lower alkyl groups containing not more than four carbon atoms, or $R_5$ and $R_6$, when taken together with the adjacent nitrogen atom, represent a ring system of the formula

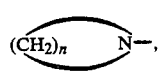

wherein n is 5, 6 or 7.

The above described composition contains the compounds of formula I and II in a weight ratio varying from 10:1 to 1:10, preferably varying from 2:1 to 1:2. Optionally, the composition can be incorporated in a pharmaceutically acceptable carrier.

It has surprisingly been found that by combining a compound with the general formula I with a compound of the general formula II to form the above described composition, the antibacterial activity of both compounds may be greatly enhanced.

A further surprising finding is that bacterial organisms may develop resistance to a combination of compounds of the formula I and II less readily than to either of the compounds alone.

In the formula I above the group R is preferably a group of the formula

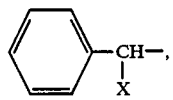

wherein X is $-H$, $-NH_2$, $-N_3$, $-COOH$ or $-SO_3H$, provided that the compound of the formula I is a penicillin. However, when the compound of the formula I above is a cephalosporin, the group R is preferably a group selected from $NC-CH_2-$, -continued

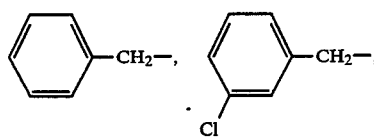

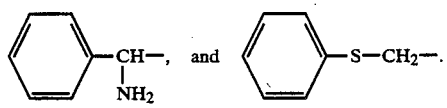

A great number of penicillins and cephalosporins with the general formula I are known to have strong antibacterial activity and such penicillins and cephalosporins have been extensively used for the treatment of infectious diseases caused by Gram-positive and Gram-negative bacteria. In the composition of the invention the preferred compounds of the formula I are the penicillins: benzyl-penicillin, 6-(D-α-amino-phenylacetamido)penicillanic acid, 6-(D-α-azido-phenylacetamido)penicillanic acid, α-carboxybenzyl-penicillin, α-hydroxysulphonyl-benzylpenicillin, and the cephalosporins which are illustrated by the specific combinations of the groups R and $R^3$ in the following table:

| R | $R_3$ | Name |
|---|---|---|
| NC—CH$_2$— | CH$_3$COO— | Cephacetrile ($R_2$ = Na) |
|  | 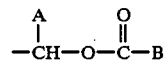 | Cephazoline ($R_2$ = Na) |
| (thiophene)-CH$_2$— | CH$_3$COO— | Cephalotine ($R_2$ = Na) |
| (phenyl)-CH(NH$_2$)— | H— | Cephalexine ($R_2$ = H) |
| (thiophene)-CH$_2$— | (pyridinium) (+) | Cephaloridine ($R_2$ = H) |
| (phenyl)-CH$_2$— | CH$_3$COO— | EPC 807/2b ($R_2$ = K) |
| (phenyl)-S—CH$_2$— | CH$_3$COO— | EPC 825/1 ($R_2$ = K) |
| (3-Cl-phenyl)-CH$_2$— | CH$_3$COO— | EPC 820/1b ($R_2$ = K) |
| (thiophene)-CH$_2$— | N$_3$— | EPC 821/4II ($R_2$ = K) | as well as the corresponding esters and salts of these penicillins and cephalosporins. In the above table, the designations R, $R_2$ and $R_3$ refer to the formula I above.

When the composition of the invention is orally administered, the penicillins or cephalosporins of the formula I may also include such known esters thereof which are rapidly hydrolyzed in vivo. Examples of such suitable ester groups i.e. the group $R_2$ in the formula I above, are acyloxy-alkyl groups, e.g. the acetoxy-methyl, the pivaloyloxy-methyl or the 1''-acetoxy-ethyl group; or alkyloxycarbonyloxy-alkyl groups e.g. the ethoxycarbonyloxymethyl or the 1'-ethoxycarbonyloxy-ethyl group.

The above mentioned suitable ester groups can be described by the formula $$-\underset{\underset{A}{|}}{CH}-O-\underset{\underset{O}{\|}}{C}-B$$

wherein A is hydrogen or methyl, and B is alkyl or alkoxy. Preferably the group B should not contain more than four carbon atoms. The preferred meaning of the group A and B is methyl and ethoxy, respectively.

Penicillin and cephalosporin esters of this type are known e.g. from German Patent Applications P 21 44 457.5; P 23 12 041.4; P 23 11 328.2; P 23 12 042.5 and P 23 11 346.4.

Penicillins of the general formula II also exhibit strong antibacterial activity, particularly against Gram-negative organisms. These until recently unknown penicillins have been described in Dutch Patent Application No. 7,016,435 and in British Patent No. 1,293,590.

Examples of compounds of the formula II are 6-[(hexahydro-1H-azepin-1-yl)methyleneamino]-penicillanic acid, 6-[(piperidyl-1)methylenamino]-penicillanic acid, 6-[(hexahydro-1(2H)-azocinnyl)methyleneamino]-penicillanic acid, and 6-[(N-ethyl-N-isopropylamino)-methyleneamino]-penicillanic acid.

In the composition of the invention the preferred penicillins of the formula II are those wherein the groups $R_5$ and $R_6$, when taken together with the adjacent nitrogen atom, represent a ring system of the formula

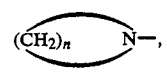

wherein n is 5, 6 or 7. Preferably n is 6.

When the composition of the invention is orally administered also the penicillin of the formula II may be in the form of a known ester thereof, which is rapidly hydrolyzed in vivo. Examples of suitable penicillin esters included in the formula II are those wherein the group $R_4$ is an acyloxy-alkyl group, e.g. the acetoxy-methyl, the pivaloyloxy-methyl or the 1''-acetoxy-ethyl group; or an alkyloxycarbonyloxy-alkyl group e.g. the ethoxycarbonyloxymethyl or the 1'-ethoxycarbonyloxyethyl group. Also these ester groups can be described by the formula

wherein A and B have the meaning given above. Penicillin esters of this type, and included in the formula II, are known e.g. from Dutch Patent Applications No. 7,016,435 and 7,303,434.

Examples of preferred penicillin esters of the formula II are pivaloyloxymethyl 6-[(hexahydro-1H-azepin-1-yl)methyleneamino]penicillanate, acetoxy-methyl 6-[(hexahydro-1H-azepin-1-yl)methyleneamino]penicillanate, pivaloyloxymethyl 6-[(hexahydro1(2H)-azocinnyl)methyleneamino]penicillanate, ethoxycarbonyloxymethyl 6-[(hexahydro-1H-azepin-1-yl)methyleneamino]penicillanate, 1'-ethoxycarbonyloxyethyl 6-[(piperidyl-1)methyleneamino]penicillanate, 1'-acetozyethyl 6-[(hexahydro-1H-azepin-1-yl)-methyleneamino]penicillanate, 1'-ethoxycarbonyloxyethyl 6-[(hexahydro1(2H)azocinnyl)methyleneamino]-penicillanate, and 1'-ethoxycarbonyloxy-ethyl 6-[(hexahydro-1H-azepin-1-yl)methyleneamino]-penicillanate, and pharmaceutically acceptable salts thereof.

The composition according to the invention can be prepared by various mixing operations well known for the preparation of compositions containing penicillins or cephalosporins. The mixing operations may be accompanied by chemical reactions between the constituents of the new composition. The mixing operations may also be combined with the simultaneous preparation of esters and salts of the penicillins and cephalosporins included in the composition of the invention. It is also to be noted that the new composition according to the invention in some respects can be regarded as one new chemical individual, as the new composition has an antibacterial activity which is unique and widely different from the acitivity which can be deduced from a calculation based upon the activity of the single constituents.

The composition of the present invention may be administered either orally or by injection. The composition may have optionally incorporated therewith other substances, e.g. pharmaceutically acceptable solid or liquid carriers or diluents and may be in any of the conventional pharmaceutical forms known to the art for penicillin therapy, for example compositions suitable for oral administration, for example tablets, granules, capsules, dispersible powders for the preparation of aqueous dispersions for oral use, solutions, suspensions or emulsions, or compositions suitable for parenteral administration, for example aqueous or non-aqueous solutions or suspensions, or dispersible powders for the preparation of sterile aqueous dispersions, or compositions suitable for topical administration, for example ointments.

The compositions according to the invention show low toxicity and are well tolerated. In the treatment of bacterial infections in man, the composition of the invention is for example administered in amounts corresponding to 5 to 200 mg/kg/day, of the active ingredients of the composition, preferably in the range of 10 to 100 mg/kg/day in divided dosages, e.g. two, three or four times a day. They are e.g. administered in dosage units containing e.g. 175, 350, 500 and 1000 mg of the active ingredients of the composition.

The following examples illustrate the remarkable antibacterial synergistical effect of the compositions according to the invention.

EXAMPLE 1

In vitro-effect of the combination of 6-(D-α-aminophenylacetamido)penicillanic acid and 6[(hexahydro-1H-azepin-1-yl)methyleneamino]penicillanic acid The in vitro activity of 6-(D-α-aminophenylacetamido) penicillanic acid (I), 6-[(hexahydro-1H-azepin-1-yl)methyleneamino]penicillanic acid (II) and of a combination (III) of equal parts of the two compounds against clinically isolated enterobacteria was determined in a serial dilution test. Tryptose phosphate broth, containing the appropriate concentrations of the compounds or of the combination of them, was inoculated with $0.5 \times 10^4$–$5 \times 10^4$ organisms of the various micro-organisms tested and incubated overnight at 37° C. Minimum inhibitory concentrations (M.I.C.) were taken as the concentrations of the compounds or of the combination at which no visible growth occurred.

| Microorganism | Strain No. | M.I.C. (µg/ml) | | |
|---|---|---|---|---|
| | | I | II | III |
| Coliform | 3/70 | 1.56 | 12.5 | 0.78 |
| Coliform | 9/70 | 3.12 | 3.12 | 0.39 |
| Coliform | 10/70 | 3.12 | 3.12 | 0.78 |
| Coliform | 17/70 | 3.12 | 0.78 | 0.39 |
| Proteus mirabilis | 35895 | 25 | 0.78 | 0.39 |
| Proteus vulgaris A | | 0.78 | 0.19 | 0.08 |
| Proteus vulgaris B | | 50 | 1.56 | 0.78 |
| Proteus | 12/70 | 100 | 3.12 | 0.78 |
| Proteus | 13/70 | 100 | 3.12 | 0.78 |
| Proteus | 20/70 | >100 | >100 | 25 |

EXAMPLE 2

In vitro-effect of combinations of 6-[(hexahydro-1H-azepin-1-yl)-methyleneamino]-penicillanic acid with various penicillins Using the same technique as described in Example 1 the in vitro-activity of 6-[(hexahydro-1H-azepin-1-yl)methyleneamino]penicillanic acid (II), of various penicillins and of 1:1-combinations of II with the respective penicillin was determined against a clinically isolated coliform bacterium (No. 9/70).

| Penicillin | M.I.C. (µg/ml) | | |
|---|---|---|---|
| | I | II | 1:1 combination |
| benzylpenicillin | 25 | 3.12 | 0.78 |
| 6-(D-α-azidophenylacetamido)penicillanic acid | 50 | 3.12 | 1.56 |
| α-carboxybenzylpenicillin | 12.5 | 3.12 | 0.38 |

EXAMPLE 3

In vivo-activity of the combination of 6-(D-α-aminophenylacetamido)penicillanic acid and 6-[(hexahydro-1H-azepin-1-yl)methyleneamino]penicillanic acid Groups of 10 animals of female NMRI white mice, 17–19 g, were given intraperitoneally inocula of the test bacterium E.coli III and immediately afterwards treated subcutaneously with the appropriate diluted aqueous solutions of 6-(D-α-aminophenylacetamido)penicillanic acid (I), 6-[(hexahydro-1H-azepin-1-yl)methyleneamino]penicillanic acid (II) and of a 1:1 combination (III) of the two compounds. The number of deaths in the various groups were recorded after 96 hours and the mean curative doses ($CD_{50}$) were calculated. (In the table, $LD_{50}$ gives the dilution of an overnight culture of the organism causing a 50% death rate in animals receiving no therapy; the number of $LD_{50}$-doses records the severity of the infections given to the animals.)

| $LD_{50}$ | $LD_{50}$-doses given | $CD_{50}$ (mg/kg) | | |
|---|---|---|---|---|
| | | I | II | III |
| $1.5 \cdot 10^{-3}$ | 6.6 | 5.5 | 2.0 | 1.0 |
| $8.1 \cdot 10^{-4}$ | $1.2 \cdot 10^4$ | 250 | >500 | 210 |

EXAMPLE 4

In vitro-effect of the combination of 6-(D-α-amino-phenylacetamido)penicillanic acid and 6[(piperidyl-1) methyleneamino]penicillanic acid Using the technique described in Example 1, the in vitro activity of 6-(D-α-aminophenylacetamido)penicillanic acid (I), 6-[(piperidyl-1)-methyleneamino]penicillanic acid (IV) and of a combination (V) of equal parts of the two compounds against clinically isolated enterobacteria was determined in serial dilution tests.

| Microorganism | Strain No. | M.I.C. (μg/ml) | | |
|---|---|---|---|---|
| | | I | IV | V |
| Coliform | 3/70 | 3.12 | 3.12 | 0.78 |
| | 7/70 | 3.12 | 1.56 | 0.78 |
| | 8/70 | 3.12 | 6.25 | 0.78 |
| | 14/70 | 6.25 | 3.12 | 1.56 |
| | 16/70 | 3.12 | 1.56 | 0.78 |
| | 17/70 | 6.25 | 1.56 | 0.78 |
| Proteus | 4/70 | 1.56 | 25 | 0.78 |
| | 6/70 | 0.39 | 3.12 | 0.18 |
| | 7/70 | 1.56 | 50 | 0.78 |
| | 9/70 | 6.25 | 100 | 1.56 |
| | 10/70 | 1.56 | 25 | 0.78 |
| Klebsiella- | 1/70 | 50 | >100 | 3.12 |
| Enterobacter. | 2/70 | 25 | 12.5 | 3,12 |
| | 5/70 | 100 | >100 | 12.5 |
| | 7/70 | >100 | >100 | 100 |
| | 9/70 | 50 | 3.12 | 1.56 |
| | 10/70 | 50 | >100 | 25 |
| | 431 | 100 | >100 | 12.5 |

EXAMPLE 5

In vitro-effect of combination of 6[(piperidyl-1)-methyleneamino]penicillanic acid (IV) with various penicillins Using the same technique as described in Example 1 the in vitro activity of 6[(piperidyl-1)-methyleneamino]penicillanic acid (IV), of various penicillins, and of 1:1 combinations of IV with these penicillins, was determined against a clinically isolated coliform bacterium.

| Penicillin | M.I.C. (μg/ml) | | |
|---|---|---|---|
| | — | IV | 1:1 combination |
| Benzylpenicillin | 25 | 6.25 | 1.56 |
| 6-(D-α-azidophenylacetamido)penicillanic acid | 50 | 6.25 | 1.56 |

| Penicillin | M.I.C. (μg/ml) | | |
|---|---|---|---|
| | — | IV | 1:1 combination |
| α-Carboxybenzylpenicillin | 12.5 | 6.25 | 1.56 |

EXAMPLE 6

Emergence of resistance for E.coli III against 6-(D-α-amino-phenylacetamido)penicillanic acid, 6-[(piperidyl-1)-methyleneamino]penicillanic acid, and a 1:1 combination of the two compounds Subculturing using a serial twofold broth dilution technique was performed with 6-(D-α-aminophenylacetamido)-penicillanic acid (I), 6-[(piperidyl-1)methyleneamino]penicillanic acid (IV) and a 1:1 combination of I+IV. As inocula were used bacteria from the tube with the highest concentration of compound still permitting visible growth to the naked eye after incubation at 37° C. overnight. The following increases in MIC-values were noted.

| Passage | MIC (μg/ml) | | |
|---|---|---|---|
| | I | IV | I + IV |
| 0 | 1.56 | 0.78 | 0.38 |
| 1 | 6.25. | 6.25 | 1.56 |
| 2 | 25 | 6.25 | 0.78 |
| 3 | 50 | 25 | 0.78 |
| 4 | 50 | 25 | 1.56 |
| 5 | 100 | 25 | 3.12 |
| 6 | 100 | 25 | 3.12 |

EXAMPLE 7

Emergence of resistance for a coliform microorganism against 6-(D-α-aminophenylacetamido)penicillanic acid, 6-[(hexahydro-1H-azepin-1-yl)methyleneamino]penicillanic acid and a combination of the two compounds Subculturing using a serial twofold broth dilution technique was performed with 6-(D-α-aminophenylacetamido)-penicillanic acid (I), 6-[(hexahydro-1H-azepin-1-yl)methyleneamino]penicillanic acid (II), and a 1:1 combination of I and II. The strain used was a clinically isolated coliform. As inocula were used bacteria from the tube with the highest concentration of compound still permitting visible growth to the naked eye after incubation at 37° C. overnight. The following increases in MIC values were noted.

| Passage | MIC (μg/ml) | | |
|---|---|---|---|
| | I | II | I + II |
| 0 | 1.56 | 0.39 | 0.38 |
| 1 | 3,12 | 6.25 | 0.78 |
| 2 | 3.12 | 25 | 0.38 |
| 3 | 6.25 | 25 | 0.78 |
| 4 | 6.25 | 25 | 0.78 |
| 5 | 6.25 | 25 | 0.78 |
| 6 | 6.25 | 12.5 | 1.56 |
| 7 | 12.5 | 25 | 1.56 |
| 8 | 12.5 | 25 | 1.56 |

EXAMPLE 8

In vitro effect of the combination of cephalotin and 6-[(N,N-diethylformamidino)-N'-amino]-penicillanic acid Using the technique described in Example 1 the in vitro activity of cephalotin (VI) and 6-[(N,N-diethylformamidino)-N'-amino]penicillanic acid (VII) and of a combination of equal parts of the compounds against clinically isolated strains of Coliforma and Klebsiella-Enterobacter was determined in serial dilution tests.

| Microorganism | Strain No. | MIC (µg/ml) | | |
|---|---|---|---|---|
| | | VI | VII | VI + VII |
| Coliforma | 3 | 6.25 | 6.25 | 1.56 |
| | 7 | 12.5 | 6.25 | 1.56 |
| | 14 | 12.5 | 12.5 | 6.25 |
| | 16 | 6.25 | 6.25 | 3.12 |
| Klebsiella-Enterobacter | 5 | 25 | >100 | 12.5 |

EXAMPLE 9

In vitro effect of combinations of 6-(D-α-aminophenylacetamido)penicillanic acid and 6-[(N,N-diethylformamidino)-N'-amino]penicillanic acid Using the technique described in Example 1 the in vitro effect of combinations of 6-(D-α-aminophenylacetamido)-penicillanic acid (I) and 6-[(N,N-diethylformamidino)-N'-amino]penicillanic acid (VII) in the ratios 1:1, 1:2 and 2:1 against clinically isolated strains of Coliforma, Klebsiella-Enterobacter and Proteus was determined in serial dilution tests.

| Microorganism | Strain No. | MIC (µg/ml) | | | | |
|---|---|---|---|---|---|---|
| | | I | VII | I + VII 1:1 | I + VII 1:2 | I + VII 2:1 |
| Coliforma | 1 | 1.56 | 3.12 | 1.56 | 0.39 + 0.78 | 0.78 + 0.39 |
| | 4 | 3.12 | 3.12 | 3.12 | 0.78 + 1.56 | 1.56 + 0.78 |
| | 7 | 1.56 | 6.25 | 3.12 | 0.78 + 1.56 | 0.78 + 0.39 |
| | 13 | 3.12 | 12.5 | 3.12 | 0.78 + 1.56 | 0.78 + 0.39 |
| | 16 | 3.12 | 6.25 | 1.56 | 0.78 + 1.56 | 0.78 + 0.39 |
| Klebsiella-Enterobacter | 1 | 50 | >100 | 12.5 | 6.25 + 12.5 | 12.5 + 6.25 |
| | 5 | 100 | >100 | 12.5 | 6.25 + 12.5 | 12.5 + 6.25 |
| | 7 | >100 | >100 | 50 | 25 + 50 | 100 + 50 |
| | 8 | 25 | 12.5 | 25 | 1.56 + 3.12 | 6.25 + 3.12 |
| Proteus | 9 | 3.12 | 100 | 3.12 | 3.12 + 6.25 | 1.56 + 0.78 |

EXAMPLE 10

In vitro effect of combinations of 6-[(hexahydro-1H-azepin-1-yl)methyleneamino]penicillanic acid with various cephalosporins Using the same technique as described in Example 1 the in vitro activity of 6-[(hexahydro-1H-azepin-1-yl)methyleneamino]penicillanic acid (II), of various cephalosporins previously mentioned in this specification, and of 1:1 combinations of II with these cephalosporins was determined against a clinically isolated strain of Klebsiella-Enterobacter (strain 4/71)

| Cephalosporin | M.I.C. (µg/ml) | | |
|---|---|---|---|
| | — | II | 1:1 combination |
| Cephacetrile | 50 | >100 | 50 |
| Cephazoline | 12.5 | >100 | 6.25 |
| Cephalotine | 50 | >100 | 6.25 |
| Cephalexine | 50 | >100 | 6.25 |
| Cephaloridine | 25 | >100 | 3.12 |
| EPC 807 2/b | >100 | >100 | 12.5 |
| EPC 825/1 | >100 | >100 | 25 |
| EPC 820/1b | >100 | >100 | 25 |
| EPC 821/4II | 100 | >100 | 6.25 |

EXAMPLE 11

In vitro effect of combinations of 6-[(hexahydro-1H-azepin-1-yl)methyleneamino]penicillanic acid with various cephalosporins Using the same technique as described in Example 1 the in vitro activity of 6-[(hexahydro-1H-azepin-1-yl)methyleneamino]penicillanic acid (II), of various cephalosporins and of 1:1 combinations of II with these cephalosporins was determined against a clinically isolated strain of Proteus (Proteus Mirabilis I 190).

| Cephalosporin | M.I.C. (µg/ml) | | |
|---|---|---|---|
| | — | II | 1:1 combination |
| Cephacetrile | 12.5 | >100 | 3.12 |
| Cephazoline | 6.25 | >100 | 0.78 |
| Cephalothine | 3.12 | >100 | 0.78 |
| Cephalexine | 25 | 100 | 1.56 |
| Cephaloridine | 6.25 | 100 | 0.78 |
| EPC 807 2/b | 25 | >100 | 3.12 |
| EPC 825/1 | 25 | >100 | 1.56 |
| EPC 820/1b | 50 | >100 | 6.25 |
| EPC 821/4II | 12.5 | >100 | 1.56 |

We claim:

1. An antibacterial combination consisting essentially of (1) a member selected from the group consisting of 6-((hexahydro-1H-azepin-1-yl)methyleneamino) penicillanic acid and its pharmaceutically acceptable easily hydrolyzable esters and pharmaceutically acceptable salts thereof and (2) a member selected from the group consisting of cephacetrile, cephazoline, cephalotine and cephalexine, and easily hydrolyzable pharmaceutically acceptable esters thereof and pharmaceutically acceptable salts thereof, said members being present in a synergistic combination in a weight ratio of from 10:1 to 1:10.

2. An antibacterial combination as in claim 1, wherein member (1) is 6-((hexahydro-1H-azepin-1-yl)methyleneamino) penicillanic acid or a pharmaceutically acceptable salt thereof.

3. An antibacterial combination as in claim 1, wherein member (1) is said ester or a salt thereof.

4. An antibacterial combination as in claim 3, wherein member (1) is the pivaloyloxymethyl ester of 6-((hexahydro-1H-azepin-1-yl)methyleneamino) penicillanic acid or a pharmaceutically acceptable salt thereof.

5. A method for the treatment of bacterial diseases which comprises administering top a warm-blooded animal suffering from such a disease, an antibacterially effective amount of (1) a member selected from the group consisting of cephacetrile, cephazoline, cephalotine and cephalexine, and easily hydrolyzable pharmaceutically acceptable esters thereof and pharmaceutically acceptable salts thereof and (2) a member which enhances the activity of said member (1) and which is selected from the group consisting of 6-((hexahydro-1H-azepin-1-yl)methyleneamino) penicillanic acid and its pharmaceutically acceptable easily hydrolyzable esters and pharmaceutically acceptable salts thereof, said members being utilized in a synergistic combination in a weight ratio of from 10:1 to 1:10.

6. A method as in claim 5, wherein the member which enhances the activity of said member (1) is 6-((hexahydro-1H-azepin-1-yl)methyleneamino) penicillanic acid or a pharmaceutically acceptable salt thereof.

7. The method of claim 5, wherein the member which enhances the activity of the said member (1) is an easily hydrolyzable pharmaceutically acceptable ester of 6-((hexahydro-1H-azepin-1-yl)methyleneamino) penicillanic acid or a pharmaceutically acceptable salt thereof.

8. A method as in claim 7, wherein the ester utilized is the pivaloyloxymethyl ester.

* * * * *

UNITED STATES PATENT AND TRADEMARK OFFICE
CERTIFICATE OF CORRECTION

PATENT NO. : 4,956,179

DATED : September 11, 1990

INVENTOR(S) : Bamberg et al.

It is certified that error appears in the above-identified patent and that said Letters Patent is hereby corrected as shown below:

Title page, Column 1, " [30] Foreign Application Data, November 1, 1971 [GB] United Kingdom 50657/71" should be -- November 1, 1971 [GB] United Kingdom 50675/71 --

Signed and Sealed this

Twelfth Day of May, 1992

Attest:

DOUGLAS B. COMER

*Attesting Officer*   *Acting Commissioner of Patents and Trademarks*